(12) United States Patent
Militzer et al.

(10) Patent No.: US 8,653,074 B2
(45) Date of Patent: Feb. 18, 2014

(54) SUBSTITUTED SODIUM 1H-PYRAZOL-5-OLATE

(75) Inventors: Hans-Christian Militzer, Odenthal (DE); Jörg Gries, Haan (DE); Stefan Koep, Ennepetal (DE)

(73) Assignee: Bayer Intellectual Property GmbH, Monheim (DE)

( * ) Notice: Subject to any disclaimer, the term of this patent is extended or adjusted under 35 U.S.C. 154(b) by 38 days.

(21) Appl. No.: 13/291,271

(22) Filed: Nov. 8, 2011

(65) Prior Publication Data

US 2012/0129857 A1 May 24, 2012

(30) Foreign Application Priority Data

Nov. 18, 2010 (DE) .......................... 10 2010 044 131

(51) Int. Cl.
*A61K 31/5377* (2006.01)
*C07D 413/14* (2006.01)

(52) U.S. Cl.
USPC ..................................... 514/236.2; 544/122

(58) Field of Classification Search
USPC ..................................... 514/236.2; 544/122
See application file for complete search history.

(56) References Cited

U.S. PATENT DOCUMENTS

| | | | |
|---|---|---|---|
| 4,075,003 A | 2/1978 | Beck et al. | |
| 4,118,574 A | 10/1978 | Beck et al. | |
| 4,663,327 A | 5/1987 | Sasse et al. | |
| 4,698,344 A | 10/1987 | Sasse et al. | |
| 4,806,540 A | 2/1989 | Sasse et al. | |
| 2003/0083351 A1 | 5/2003 | Almstead et al. | |
| 2006/0067927 A1 | 3/2006 | Chandrasekaran et al. | |
| 2006/0160826 A1 | 7/2006 | Ghanbari et al. | |
| 2010/0035906 A1 | 2/2010 | Flamme et al. | |
| 2010/0093803 A1 | 4/2010 | Thede et al. | |
| 2010/0305085 A1 | 12/2010 | Thede et al. | |

FOREIGN PATENT DOCUMENTS

| | | |
|---|---|---|
| CA | 1067907 A1 | 6/1977 |
| CA | 2364908 A1 | 9/2000 |
| CA | 2608099 A2 | 11/2006 |
| CA | 2667392 | 2/2008 |
| WO | 96/12706 A1 | 5/1996 |
| WO | 02/092573 A2 | 11/2002 |
| WO | 03/051833 A2 | 6/2003 |
| WO | 03/074550 A2 | 9/2003 |
| WO | 2004/052284 | 6/2004 |
| WO | 2004/087066 | 10/2004 |
| WO | 2004/089303 A2 | 10/2004 |
| WO | 2005/030121 | 4/2005 |
| WO | 2006/101903 A1 | 9/2006 |
| WO | 2007/008541 A2 | 1/2007 |

OTHER PUBLICATIONS

Hill et al. "Inhibition of TRPM2 channels by the antifungal agents clotrimazole and econazole," Naunyn Schmiedebergs Arch. Pharmacol, 2004, 370: 277-238.
R.I Dowell et al.: Novel Inhibitore of Prolyl 4-hydroxylase: Part 4. Pyridine-2-Carboxylic Acid Analogues with Alternative 2-Substituents,: Eur. J. Med. Chem, 1993, 25:513-516.
Ulrich, "Crystallization: 4. Crystal Characteristics," Kirk-Othmer Encyclopedia of Chemical Technology, Aug. 2002.
M. Simmons et al., "Therapeutic Angiogenesis in Cardiovascular Disease," Nat. Rev. Drug Discovery, 2003, 2(11): 1-9.
K-U Eckardt, "The potential of erytropoeitin and related strategies to stimulate erytropoiesis," Current Opinion in Investigational Drugs, 2001, 2(8):1081-1085.
J.S. Berns, "Should the target hemoglobin for patients with chronic kidney disearse treated with erytropoietic replacement therapy be changed?" Seminars in Dialysis, Jan.-Feb. 2005, 18(1):22-29.
K. Caiola et al., "Use of erythropoietin in heart failure management," The Annals of Pharmacotherapy, Dec. 2004, 38:2145-2149.
S.D. Katz, "Mechanisms and treatment of anemia in chronic heart failure," Cong Heart Failure, 2004, 10: 243-247.
G. L. Semenza: "Hypoxia-Inducible Factor 1: Oxegyn Homeostasis and Disease Pathophysiology," Trends in Molecular Medicine, Aug. 2001, 7(8): 345-350.
R.H. Wenger et al.: "Oxygen(es) and the Hpyoxia-Inducible Factor-1," Biol. Chem., Jul. 1997, 378: 609-616.
A.C.R. Epstein et al.: "*C. elegans* EGL-9 and Mammalian Homologs Define a Family of Dioxygenases that Regulate HIF by Prolyl Hydroxylation," Cell, Oct. 5, 2001, 107: 43-54.
R.K. Bruick et al.: "A Conserved Family of Prolyl-4-Hydroxylases that Modify HIF," Science 294, Nov. 9, 2001, pp. 1337-1340.
M. Ivan et al.: "Biochemical Purification and Pharmacological Inhibition of a Mammalian Prolyl Hydroxylase Acting on Hypoxia-Inducible Factor," Proc. Natl. Acad. Sci, Oct. 15, 2001, 99(21): 13459-13464.
L. Aravind et al.: "The DNA-Repair Protein AlkB, EGL-9, and Leprecan Define New Families of 2-Oxoglutarate- and Iron-Dependent Dixygenases," Genome Biology, Feb. 19, 2001, 2(3): 1-8.
C.J. Schofield et al.: "Oxygen Sensing by HIF Hydrixylases," Nature Reviews Molecular Cell Biology, May 2004, 5:343-354.
J. Büchi et al.: "Synthese und Pharmakologische Eigenschaften Einiger Pyridyl-Pyrazol-5-one," Helv. Chim. Acta, 1996, 49(1): 272-280.
B. Djerrari et al.: "3-Methyl-1-(Pyridin-2-yl)-4-(1-Pyridin-2-yl-3-Methyl-1H-Pyrazol-5-yl)-2H-3-Pyrazolin-5(1Hl)-one," Acta Crystallographica Section E, Structure Reports Online, 2001, E57, No. 11, pp. o1126-o1127.

(Continued)

*Primary Examiner* — Kristin Vajda
(74) *Attorney, Agent, or Firm* — Karen B. King

(57) ABSTRACT

The present application relates to sodium 1-[6-(morpholin-4-yl)pyrimidin-4-yl]-4-(1H-1,2,3-triazol-1-yl)-1H-pyrazol-5-olate, to processes for its preparation, to its use for the treatment and/or prophylaxis of diseases and to its use for the preparation of medicaments for the treatment and/or prophylaxis of diseases, in particular cardiovascular and haematological diseases and kidney diseases, and for promoting wound healing.

9 Claims, 10 Drawing Sheets

(56) References Cited

OTHER PUBLICATIONS

S.P. Singh et al.: "Reaction of 1-[5-Hydroxy-3-Methyl-1-(2-Thiazolyl)-4-Pyrazolyl]-1,3-Butanediones with Phenyl and Heterocyclic Hydrazines: a Convienient Syntheses of 4,5-Bipyrazoles," Indian Journal of Heterocyclic Chemistry, Jul.-Sep. 1993, 3: 5-8.

J. Elguero et al.: "A 1H and 13C NMR Study of the Structure and Tautomerism of 4-Pyrazolylprazolinones," J. Heterocyclic Chem., May-Jun. 1990, 27: 865-870.

H. Barth et al.: "Konstitution und Synthese des Muscafavins," Liebigs Ann. Chem., 1981, pp. 2164-2179.

R.A. Evans et al.:"Trifluromethyl-substituted Dehydrodizepines and Cyanopyrroles form Azido-/Tetrazolo-pyridines," J. Chem. Commun., 1992, 15: 1062-1064.

F. Oehme et al.: "A Nonradioactive 96-well Plate Assay for the Detection of Hypozia-Inducible Factor Prolyl Hydroxylase Activity," Analytical Biochemistry, 2004, 330: 74-80.

F. Oehme et al.: "Overexpression of PH-4, a Novel Putative Proline 4-Hydroxylase, Modulates Activity of Hypoxia-Inducible Transcription Factors, "Biochemical and Biophysical Research Communications, 2002, 296: 343-349.

C.A. Heid et al.: "Real Time Quantative PCR," Genome Research, 1996, 6(10): 986-994.

N. Yokoyama et al.: Synthesis and Structure-Activity Relationships of Oxamic Acid and Acetic Acid Derivatives Released to L-Thyronine,: J. Med. Chem., 1995, 38:695-707.

N. Sperber er al.: "Parasympathetic Blocking Agernt, III. N-Alkylpiperidinecarboxylic Esters," J. AM. Chem. Soc, 1959, 81: 704-709.

M.A. Meziane et al.: "A New Route to 1-Oxo-1,2-Dihydropyrimido[1,6-a]Benzimidazole-4-Carboxylates from Ethyl 2-(Benzimidazol-2-yl)-3-(Dimethylamino)Acrylate Using Solvent-Free Conditions," Synthesis, Jul. 1996, pp. 967-969.

Vippagunta et al., "Crystalline Solids," Advanced Drug Delivery Reviews, 2001, 48: 3-26.

West, "Solid Solutions," 1988, Chapter 10, pp. 358 and 365.

U.S. Appl. No. 12/427,749, filed Apr. 22, 2009, now US Patent No. 8,067,407.

U.S. Appl. No. 12/447,207, filed Dec. 21, 2009.

U.S. Appl. No. 12/447,201, filed Oct. 26, 2007.

U.S. Appl. No. 11/919,478, filed Oct. 30, 2009.

U.S. Appl. No. 12/447,192, filed Oct. 12, 2007.

Fig. 1 IR spectra of the compound of the formula (II) and of the compound of the formula (I)
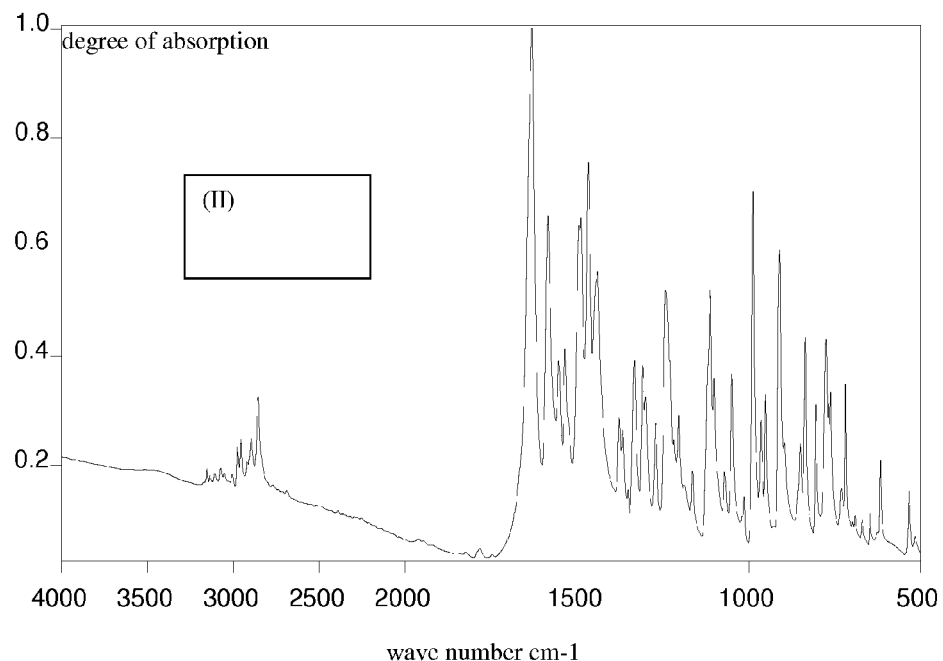
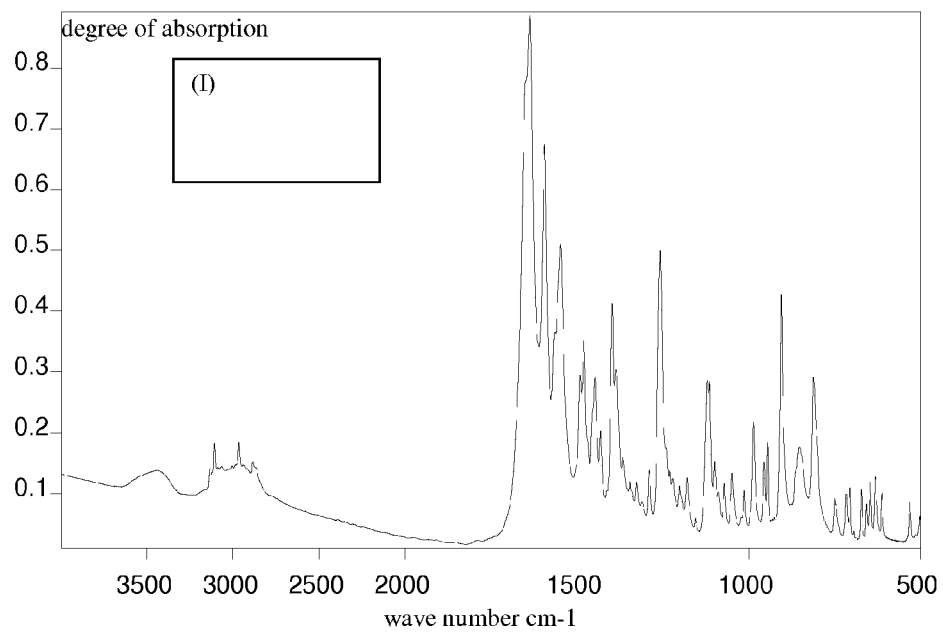

Fig. 2 Raman spectra of the compound of the formula (II) and of the compound of the formula (I)
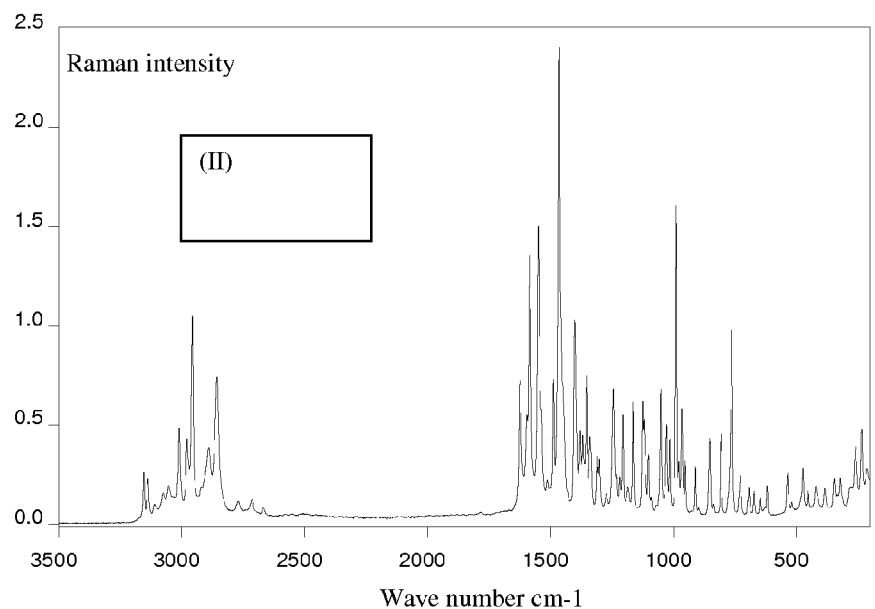
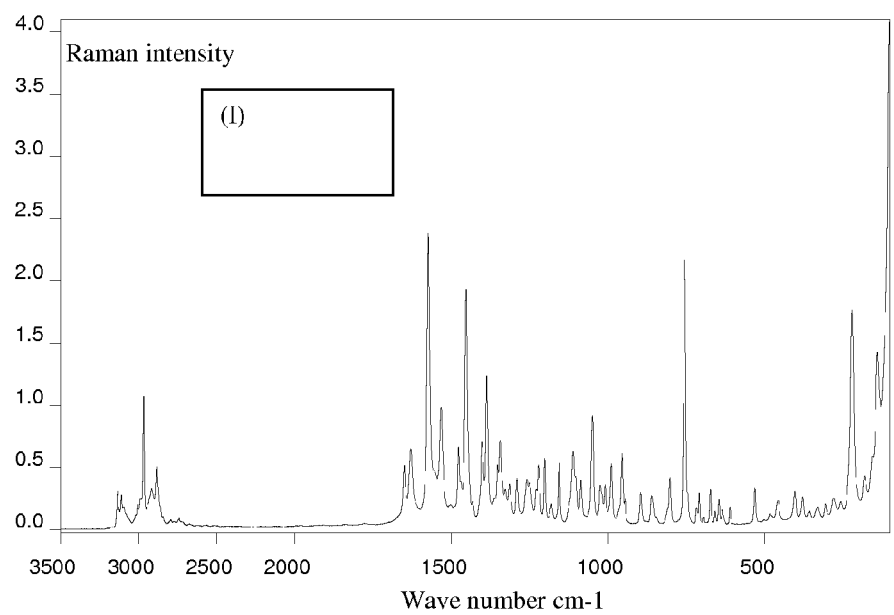

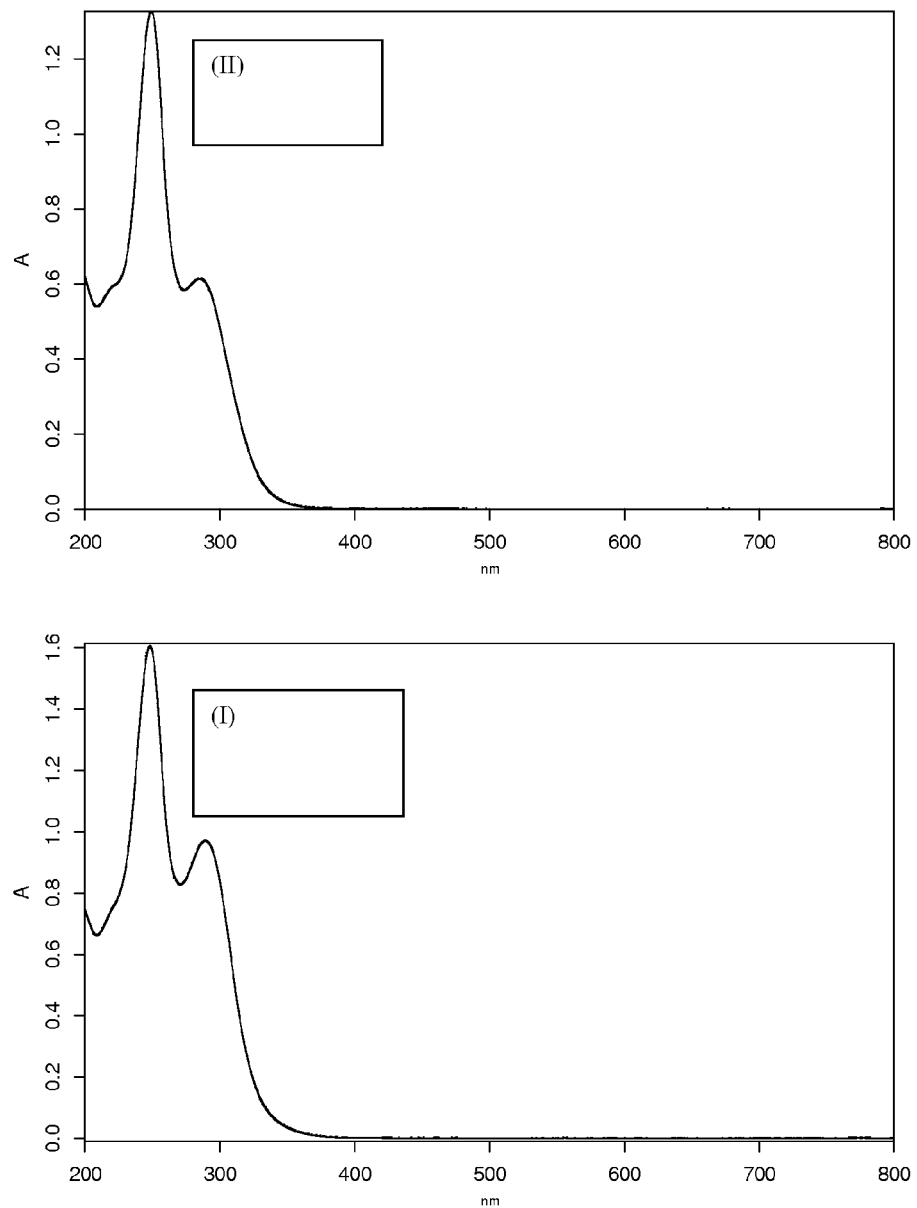
Fig. 3 UV/VIS spectra of the compound of the formula (II) and of the compound of the formula (I)

Fig. 4: ¹H NMR spectrum of the compound of the formula (II)
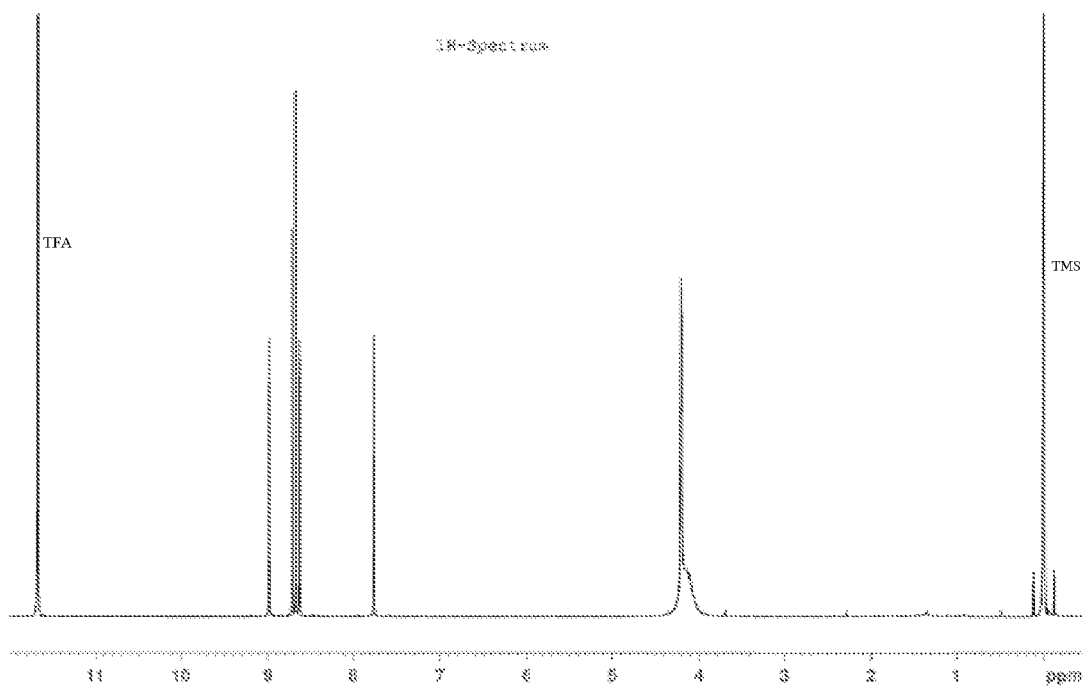

Fig. 5: $^1$H NMR spectrum of the compound of the formula (I)
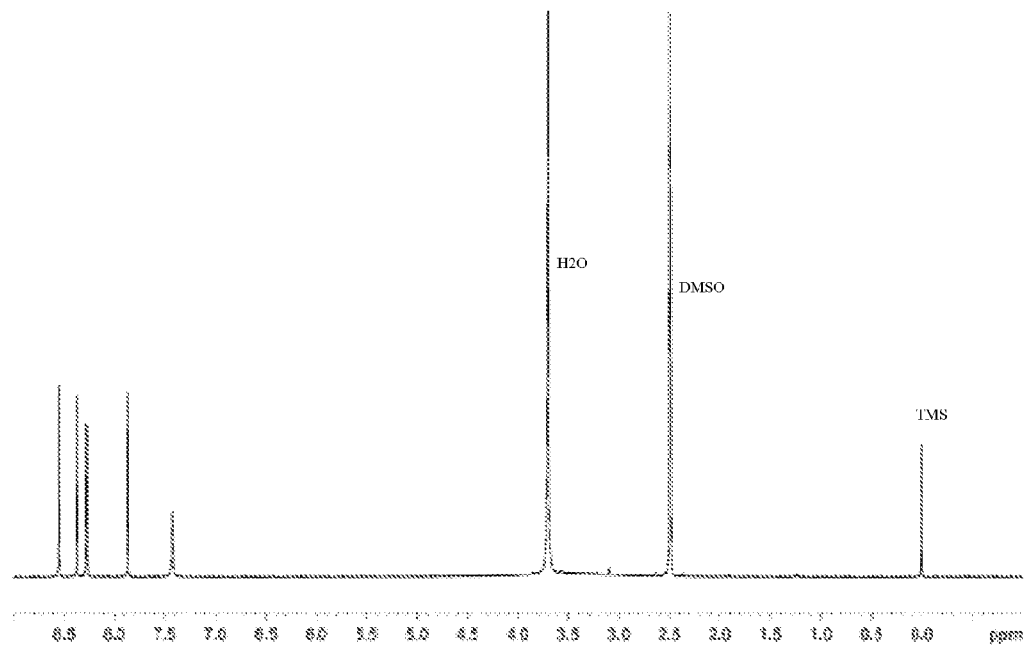

Fig. 6: $^{13}$C NMR spectrum of the compound of the formula (II)
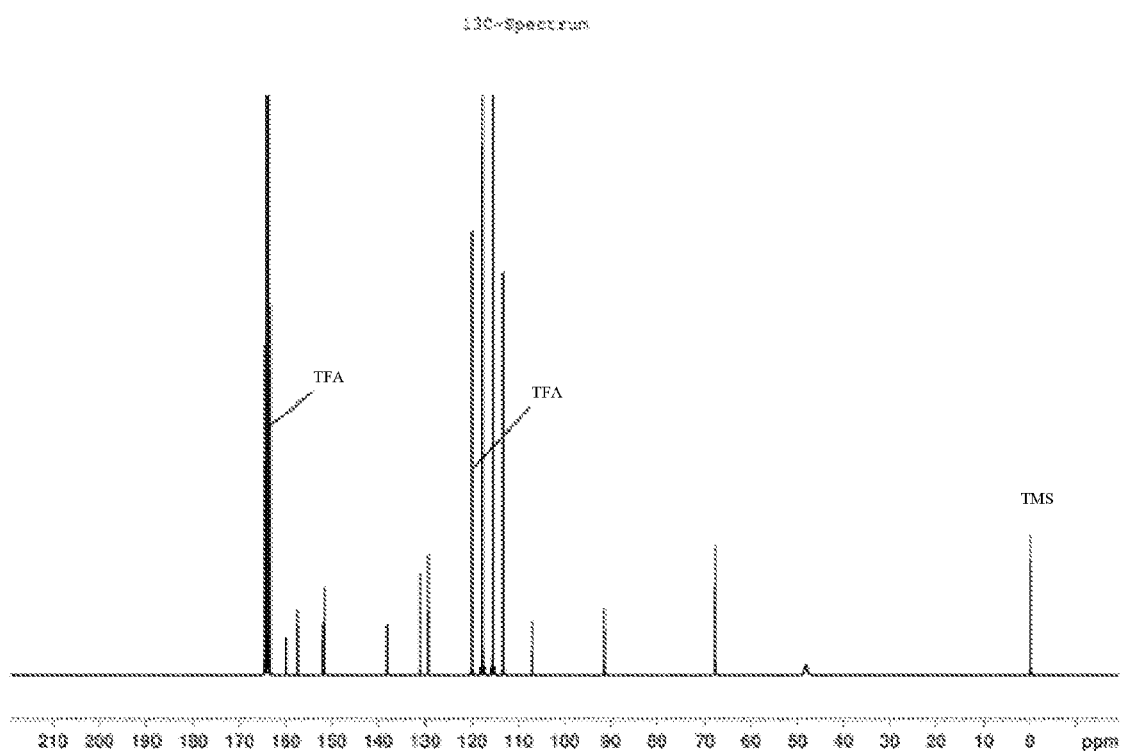

Fig. 7: $^{13}$C NMR spectrum of the compound of the formula (I)
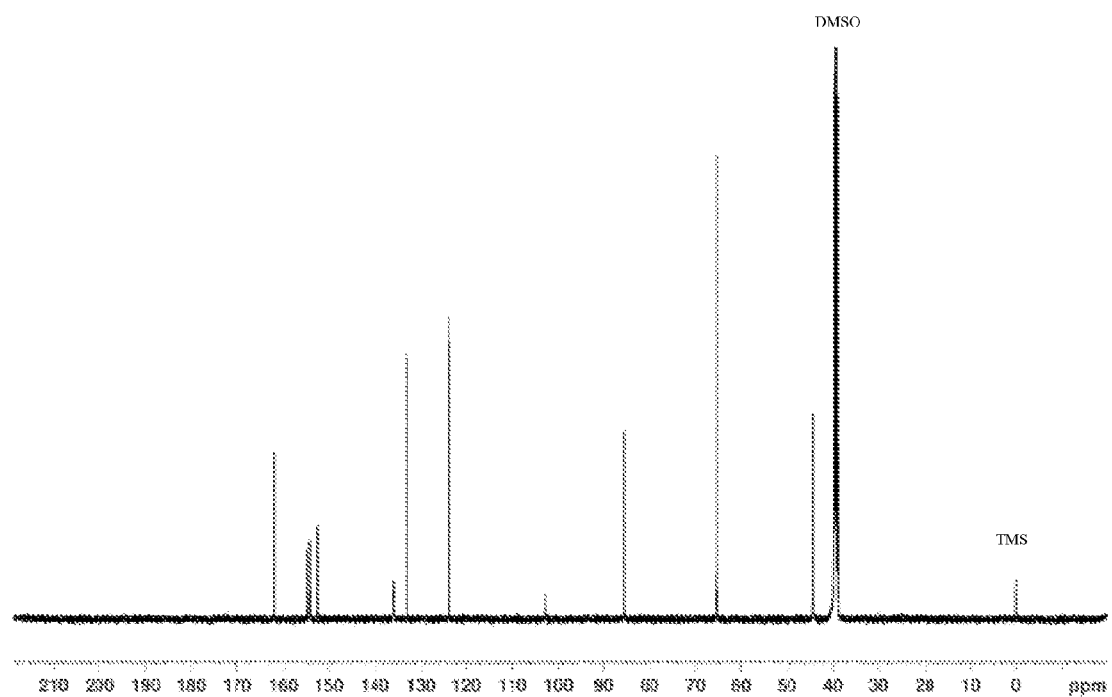

Fig. 8: Mass spectrum of the compound of the formula (II)
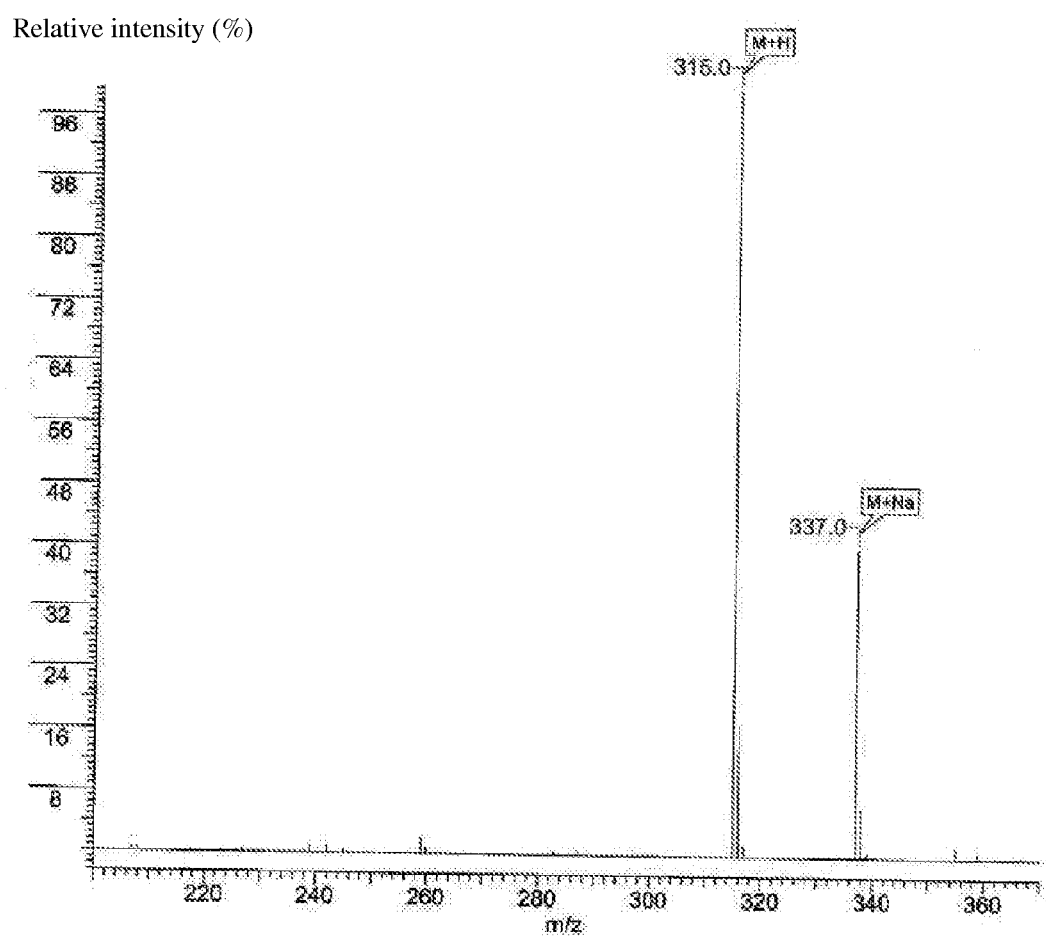

Fig. 9: Mass spectrum of the compound of the formula (I)
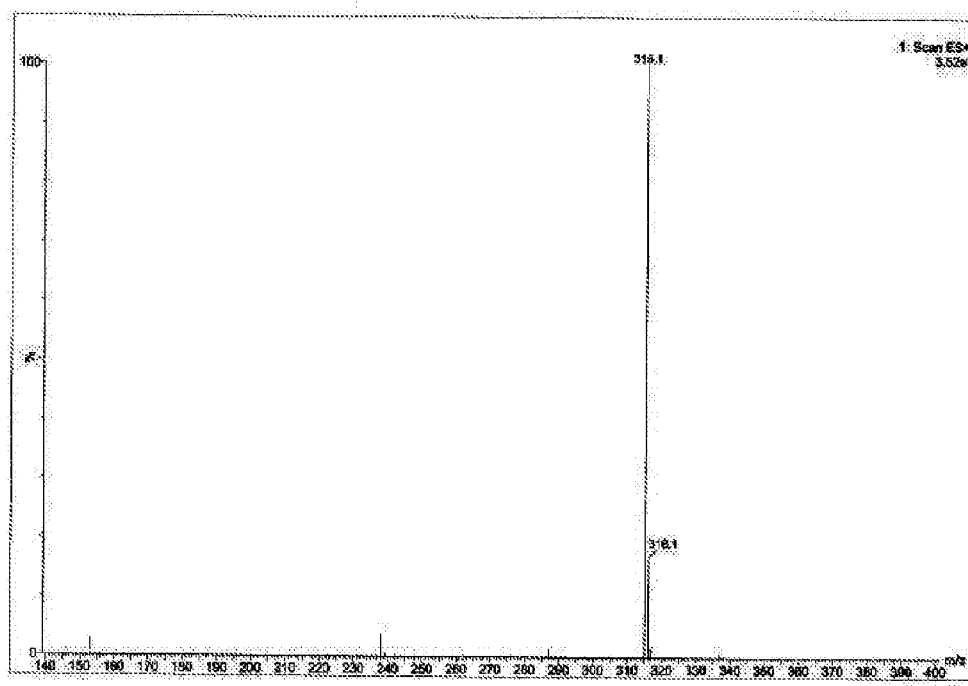
Fig. 10: X-ray diffractogramm of the compound of the formula (II)
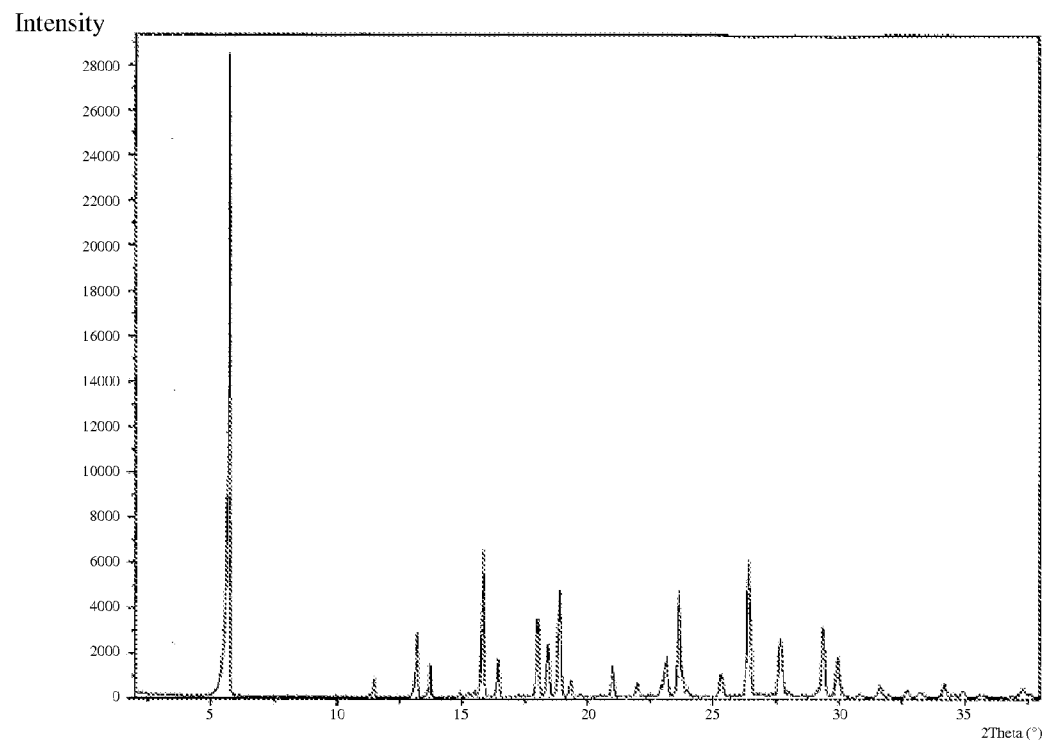

Fig. 11: X-ray diffractogramm of the compound of the formula (I)
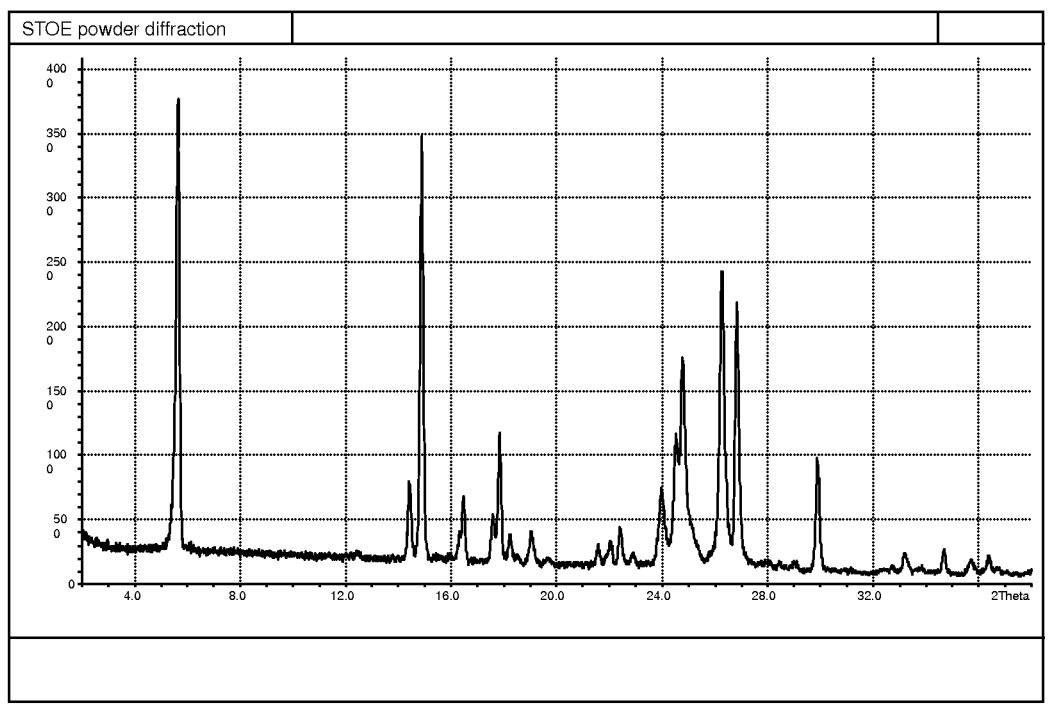

SUBSTITUTED SODIUM 1H-PYRAZOL-5-OLATE

The present application relates to sodium 1-[6-(morpholin-4-yl)pyrimidin-4-yl]-4-(1H-1,2,3-triazol-1-yl)-1H-pyrazol-5-olate, to processes for its preparation, to its use for the treatment and/or prophylaxis of diseases and to its use for the preparation of medicaments for the treatment and/or prophylaxis of diseases, in particular cardiovascular and haematological diseases and kidney diseases, and for promoting wound healing.

The compound of the formula (I), 1-[6-(morpholin-4-yl)pyrimidin-4-yl]-4-(1H-1,2,3-triazol-1-yl)-1H-pyrazol-5-ol (enol form; formula (Ia)) or 2-[6-(morpholin-4-yl)pyrimidin-4-yl]-4-(1H-1,2,3-triazol-1-yl)-1,2-dihydro-3H-pyrazol-3-one (keto form; formula (Ib)), is known from WO 2008/067871.

The present invention provides the compound sodium 1-[6-(morpholin-4-yl)pyrimidin-4-yl]-4-(1H-1,2,3-triazol-1-yl)-1H-pyrazol-5-olate, which corresponds to the compound of the formula (II)

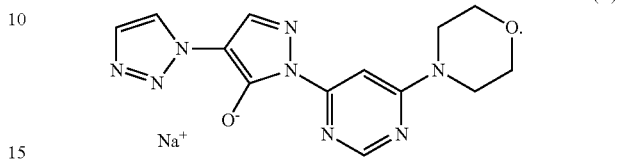

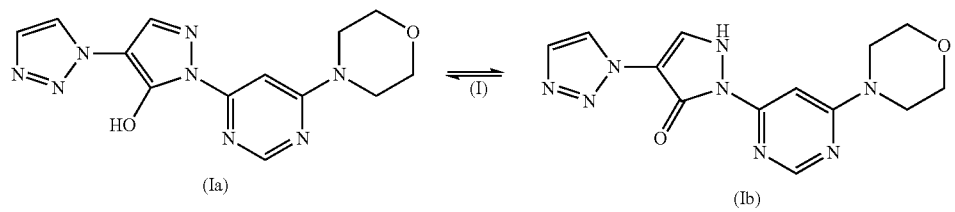 [SMILES: Oc1c(-n2ccnn2)cnn1-c1cc(N2CCOCC2)ncn1 ; "(I)" ; O=c1c(-n2ccnn2)c[nH]n1-c1cc(N2CCOCC2)ncn1]

The compound of the formula (I) acts as an inhibitor of HIF-prolyl-4-hydroxylases and, as a result of this specific mechanism of action, induces, after parenteral or oral administration, the in vivo induction of HIF target genes such as, for example, erythropoietin, and of the biological processes triggered thereby, such as, for example, erythropoiesis.

The compound of the formula (I) is hygroscopic and, at customary environmental conditions (20-35° C., atmospheric pressure), takes up up to about 6% by weight of water even at a relative atmospheric humidity above 20% rh. At an atmospheric humidity of 30% rh, the uptake of 6% by weight of water is almost complete. If the atmospheric humidity decreases below 30% rh, the compound of the formula (I) releases part of the water it comprises. This uptake of water or release of water renders handling of the compound of the formula (I), for example weighing operations, and the production of the compound of the formula (I) in a uniform, stable and defined form for use in medicaments or the production of medicaments comprising compound of the formula (I) more difficult. In particular, this increases the technical expenditure during the production of administration forms comprising the compound of the formula (I), such as, for example, tablets, granules or drink solutions, since measures for controlling and regulating atmospheric humidity are required to maintain a uniform concentration of the compound of the formula (I).

It has now been found that it is possible to prepare from the compound of the formula (I) a sodium salt which, compared to the compound of the formula (I), has decisive advantages.

In the context of the present invention, sodium 1-[6-(morpholin-4-yl)pyrimidin-4-yl]-4-(1H-1,2,3-triazol-1-yl)-1H-pyrazol-5-olate (compound of the formula (II)) is preferably present in crystalline form.

The use according to the invention of the compound of the formula (II) ensures that, compared to the known compound of the formula (I), a significantly higher stability with respect to the uptake or release of water is achieved in cases of varying atmospheric humidity. Sodium 1-[6-(morpholin-4-yl)pyrimidin-4-yl]-4-(1H-1,2,3-triazol-1-yl)-1H-pyrazol-5-olate (compound of the formula (II)) comprises less than 0.5% by weight of water and is not hygroscopic, and under customary environmental conditions (20-35° C., atmospheric pressure) even at an elevated atmospheric humidity of up to 90% rh its water content changes only to a minimal extent, i.e. by less than 0.5% by weight. Technically, i.e. during weighing operations and in particular in cases where a uniform concentration of the compound of the formula (II) in an administration form such as, for example, granules, a drink solution or a tablet, has to be ensured, the compound of the formula (II) is considerably easier to handle. In addition, compared to the compound of the formula (I) the compound of the formula (II) has a higher solubility in water.

The invention furthermore provides a process for preparing the compound of the formula (II) according to the invention, characterized in that the compound of the formula (I)

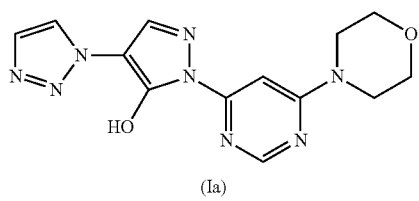
(Ia)

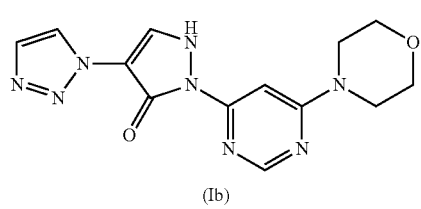
(Ib)

is reacted in a solvent with sodium hydroxide or aqueous sodium hydroxide solution or a sodium salt, if appropriate with addition of a base.

Preference is given to a process for preparing the compound of the formula (II) according to the invention which is characterized in that the compound of the formula (I) is reacted in a solvent with aqueous sodium hydroxide solution, if appropriate with addition of a base.

Particular preference is given to a process for preparing the compound of the formula (II) according to the invention which is characterized in that the compound of the formula (I) is reacted in a solvent with aqueous sodium hydroxide solution with addition of triethylamine.

The reaction with sodium hydroxide or aqueous sodium hydroxide solution or a sodium salt is generally carried out in a solvent, preferably in a temperature range of from 20° C. to 120° C., particularly preferably in a temperature range of from 40° C. to 70° C., at atmospheric pressure. From the suspension obtained, the compound of the formula (II) is isolated by filtration at a temperature between −20° C. and 80° C., preferably at a temperature of from 0° C. to 20° C., at atmospheric pressure, and it is subsequently dried.

If the reaction is carried out with addition of a base, the compound of the formula (I) is generally first dissolved with addition of an organic base in a solvent at a temperature of from 20° C. to 120° C., preferably at a temperature of from 40° C. to 70° C., at atmospheric pressure, and the compound of the formula (II) is then precipitated by addition of sodium hydroxide or aqueous sodium hydroxide solution or a sodium salt at a temperature of from 20° C. to 120° C., preferably at a temperature of from 40° C. to 70° C., at atmospheric pressure. From the suspension obtained, the compound of the formula (II) is isolated by filtration at a temperature between −20° C. and 80° C., preferably at a temperature of from 0° C. to 20° C., at atmospheric pressure, and it is subsequently dried.

Sodium hydroxide and aqueous sodium hydroxide solution and the sodium salt are employed in a molar ratio of from 0.8 to 2 molar equivalents with respect to the compound of the formula (I). Preferably, sodium hydroxide and aqueous sodium hydroxide solution and the sodium salt are employed in a molar ratio of from 1.0 to 1.4 molar equivalents with respect to the compound of the formula (I).

Suitable sodium salts are, for example, salts of organic acids such as sodium carboxylates, such as, for example, sodium acetate or sodium citrate, or salts or inorganic acids such as, for example, sodium carbonate, sodium bicarbonate, sodium phosphate, sodium hydrogenphosphate or sodium chloride.

Suitable solvents are lower alcohols such as, for example, methanol, ethanol, n-propanol, isopropanol, n-butanol, sec-butanol, isobutanol, 1-pentanol, or tetrahydrofuran, or acetonitrile, or toluene, or 1,4-dioxane or mixtures of the solvents mentioned, or mixtures of the solvents mentioned with water. Preference is given to methanol, ethanol, 2-propanol, tetrahydrofuran or mixtures of the solvents mentioned with water.

Particular preference is given to mixtures of methanol with water or ethanol with water in a ratio between 1:1 and 50:1 (v/v), very particular preference is given to mixtures of methanol with water in a ratio between 7:3 and 30:1 (v/v).

Suitable organic bases are tertiary amines such as, for example, triethylamine or diisopropylethylamine. Preference is given to triethylamine. The organic base is employed in a ratio of from 0 to 4 molar equivalents with respect to the compound of the formula (I). Preferably, the organic base is employed in a ratio of from 0.7 to 1.5 molar equivalents with respect to the compound of the formula (I).

The preparation of the compound of the formula (II) according to the invention can be illustrated by the reaction scheme below:

Scheme

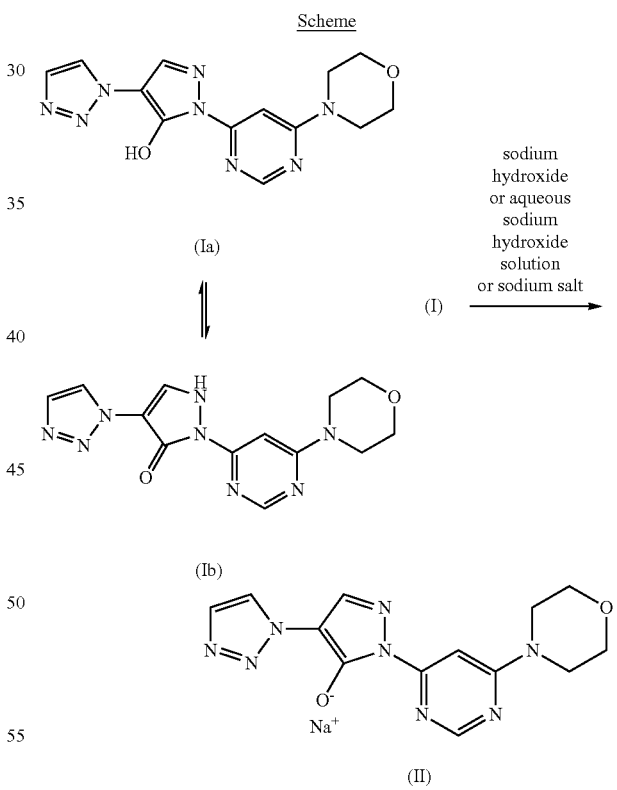

EXPLANATION OF THE FIGURES

FIG. 1: IR spectra of the compound of the formula (II) and of the compound of the formula (I)

FIG. 2: Raman spectra of the compound of the formula (II) and of the compound of the formula (I)

FIG. 3: UV/VIS spectra of the compound of the formula (II) and of the compound of the formula (I)

FIG. 4: $^1$H NMR spectrum of the compound of the formula (II)

FIG. 5: $^1$H NMR spectrum of the compound of the formula (I)

FIG. 6: $^{13}$C NMR spectrum of the compound of the formula (II)

FIG. 7: $^{13}$C NMR spectrum of the compound of the formula (I)

FIG. 8: Mass spectrum of the compound of the formula (II)

FIG. 9: Mass spectrum of the compound of the formula (I)

FIG. 10: X-ray diffractogram of the compound of the formula (II)

FIG. 11: X-ray diffractogram of the compound of the formula (I)

The compound of the formula (II) according to the invention shows an unforeseeable, useful spectrum of pharmacological action. It is therefore suitable for use as medicaments for the treatment and/or prophylaxis of diseases in humans and animals The compound of the formula (II) according to the invention is distinguished as a specific inhibitor of HIF prolyl 4-hydroxylases.

On the basis of its pharmacological properties, the compound of the formula (II) according to the invention can be employed for the treatment and/or prophylaxis of cardiovascular diseases, in particular cardiac insufficiency, coronary heart disease, angina pectoris, myocardial infarction, stroke, arteriosclerosis, essential, pulmonary and malignant hypertension and peripheral arterial occlusive disease.

The compound of the formula (II) according to the invention is furthermore suitable for the treatment and/or prophylaxis of blood formation disorders, such as, for example, idiopathic anaemias, renal anaemia and anaemias accompanying a tumour disease (in particular an anaemia induced by chemotherapy), an infection (in particular HIV infection) or another inflammatory disease, such as, for example, rheumatoid arthritis. The compound of the formula (II) according to the invention is moreover suitable for supporting treatment of anaemias as a result of blood loss, iron deficiency anaemia, vitamin deficiency anaemia (e.g. as a result of vitamin B12 deficiency or as a result of folic acid deficiency), hypoplastic and aplastic anaemia or haemolytic anaemia, or for supporting treatment of anaemias as a result of iron utilization disorders (sideroachrestic anaemia) or anaemias as a result of other endocrine disorders (e.g. hypothyroidosis).

The compound of the formula (II) according to the invention is furthermore suitable for increasing the haematocrit with the aim of obtaining blood for autodonation of blood before operations.

The compound of the formula (II) according to the invention can moreover be used for the treatment and/or prophylaxis of operation-related states of ischaemia and consecutive symptoms thereof after surgical interventions, in particular interventions on the heart using a heart-lung machine (e.g. bypass operations, heart valve implants), interventions on the carotid arteries, interventions on the aorta and interventions with instrumental opening or penetration of the skull cap. The compound of the formula (II) according to the invention is furthermore suitable for general treatment and/or prophylaxis in the event of surgical interventions with the aim of accelerating wound healing and shortening the convalescence time.

The compound of the formula (II) according to the invention is moreover suitable for the treatment and prophylaxis of consecutive symptoms of acute and protracted ischaemic states of the brain (e.g. stroke, birth asphyxia).

The compound of the formula (II) according to the invention can furthermore be employed for the treatment and/or prophylaxis of cancer and for the treatment and/or prophylaxis of an impairment in the state of health occurring in the course of treatment of cancer, in particular after therapy with cytostatics, antibiotics and irradiations.

The compound of the formula (II) according to the invention is furthermore suitable for the treatment and/or prophylaxis of diseases of the rheumatic type and other disease forms to be counted as autoimmune diseases, and in particular for the treatment and/or prophylaxis of an impairment in the state of health occurring in the course of medicamentous treatment of such diseases.

The compound of the formula (II) according to the invention can moreover be employed for the treatment and/or prophylaxis of diseases of the eye (e.g. glaucoma), the brain (e.g. Parkinson's disease, Alzheimer's disease, dementia, chronic pain sensation), of chronic kidney diseases, renal insufficiency and acute renal failure and for promoting wound healing.

The compound of the formula (II) according to the invention is moreover suitable for the treatment and/or prophylaxis of general physical weakness, up to cachexia, in particular occurring to an increased extent at a more elderly age.

The compound of the formula (II) according to the invention is furthermore suitable for the treatment and/or prophylaxis of sexual dysfunction.

The compound of the formula (II) according to the invention is moreover suitable for the treatment and/or prophylaxis of diabetes mellitus and its consecutive symptoms, such as, for example, diabetic macro- and microangiopathy, diabetic nephropathy and neuropathy.

The compound of the formula (II) according to the invention is moreover suitable for the treatment and/or prophylaxis of fibrotic diseases of the heart, the lungs and the liver, for example.

In particular, the compound of the formula (II) according to the invention is also suitable for prophylaxis and treatment of retinopathy in premature babies (retinopathia prematurorum).

The present invention moreover provides the use of the compound of the formula (II) according to the invention for the treatment and/or prevention of diseases, in particular the abovementioned diseases.

The present invention moreover provides the use of the compound of the formula (II) according to the invention for the preparation of a medicament for the treatment and/or prevention of diseases, in particular the abovementioned diseases.

The present invention moreover provides a method for the treatment and/or prevention of diseases, in particular the abovementioned diseases, using an active amount of the compound of the formula (II) according to the invention.

The compound of the formula (II) according to the invention can be employed by itself or, if required, in combination with other active compounds. The present invention moreover provides medicaments comprising the compound of the formula (II) according to the invention and one or more further active compounds, in particular for treatment and/or prevention of the abovementioned diseases. Suitable active compounds in the combination which may be mentioned by way of example and preferably are: ACE inhibitors, angiotensin II receptor antagonists, beta receptor blockers, calcium antagonists, PDE inhibitors, mineralocorticoid receptor antagonists, diuretics, aspirin, iron supplements, vitamin B12 and folic acid supplements, statins, digitalis (digoxin) derivatives, tumour chemotherapeutics and antibiotics.

In a preferred embodiment of the invention, the compound of the formula (II) according to the invention is administered in combination with an ACE inhibitor, such as, by way of example and preferably, enalapril, captopril, lisinopril, ramipril, delapril, fosinopril, quinopril, perindopril or trandopril.

In a preferred embodiment of the invention, the compound of the formula (H) according to the invention is administered in combination with an angiotensin AII antagonist, such as, by way of example and preferably, losartan, candesartan, valsartan, telmisartan or embusartan.

In a preferred embodiment of the invention, the compound of the formula (H) according to the invention is administered in combination with a beta receptor blocker, such as, by way of example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compound of the formula (H) according to the invention is administered in combination with a calcium antagonist, such as, by way of example and preferably, nifedipine, amlopidine, verapamil or diltiazem.

In a preferred embodiment of the invention, the compound of the formula (H) according to the invention is administered in combination with a phosphodiesterase (PDE) inhibitor, such as, by way of example and preferably, milrinone, amrinone, pimobendan, cilostazol, sildenafil, vardenafil or tadalafil.

In a preferred embodiment of the invention, the compound of the formula (H) according to the invention is administered in combination with a mineralocorticoid receptor antagonist, such as, by way of example and preferably, spironolactone, eplerenone, canrenone or potassium canrenoate.

In a preferred embodiment of the invention, the compound of the formula (H) according to the invention is administered in combination with a diuretic, such as, by way of example and preferably, furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerine, isosorbide, mannitol, amiloride or triamterene.

In a preferred embodiment of the invention, the compound of the formula (II) according to the invention is administered in combination with an HMG-CoA reductase inhibitor from the class of statins, such as, by way of example and preferably, lovastatin, simvastatin, pravastatin, fluvastatin, atorvastatin, rosuvastatin, cerivastatin or pitavastatin.

In a preferred embodiment of the invention, the compound of the formula (II) according to the invention is administered in combination with a tumour chemotherapeutic, by way of example and preferably from the group consisting of platinum complexes, such as, for example, cisplatin and carboplatin, the alkylating agents, such as, for example, cyclophosphamide and chlorambucil, the antimetabolites, such as, for example, 5-fluorouracil and methotrexate, the topoisomerase inhibitors, such as, for example, etoposide and camptothecin, the antibiotics, such as, for example, doxorubicin and daunorubicin, or the kinase inhibitors, such as, for example, sorafenib and sunitinib.

In a preferred embodiment of the invention, the compound of the formula (II) according to the invention is administered in combination with an antibiotic, by way of example and preferably from the group consisting of penicillins, cephalosporins or quinolones, such as, for example, ciprofloxacin and moxifloxacin.

The present invention moreover provides medicaments which comprise the compound of the formula (II) according to the invention, conventionally together with one or more inert, non-toxic, pharmaceutically suitable auxiliary substances, and the use thereof for the abovementioned purposes.

The compound of the formula (II) according to the invention can act systemically and/or locally. They can be administered in a suitable manner for this purpose, such as, for example, orally, parenterally, pulmonally, nasally, sublingually, lingually, buccally, rectally, dermally, transdermally, conjunctivally, otically or as an implant or stent.

For these administration routes, the compound of the formula (II) according to the invention can be administered in suitable administration forms.

Administration forms which function according to the prior art, release the compound of the formula (II) according to the invention rapidly and/or in a modified manner and comprise the compounds according to the invention in crystalline and/or amorphized and/or dissolved form are suitable for oral administration, such as, for example, tablets (noncoated or coated tablets, for example coatings which are resistant to gastric juice or dissolve in a delayed manner or are insoluble and control the release of the compound according to the invention), tablets or films/oblates, films/lyophilizates or capsules which disintegrate rapidly in the oral cavity (for example hard or soft gelatin capsules), sugar-coated tablets, granules, pellets, powders, emulsions, suspensions, aerosols or solutions.

Parenteral administration can be effected with bypassing of an absorption step (e.g. intravenously, intraarterially, intracardially, intraspinally or intralumbarly) or with inclusion of an absorption (e.g. intramuscularly, subcutaneously, intracutaneously, percutaneously or intraperitoneally). Administration forms which are suitable for parenteral administration are, inter alia, injection and infusion formulations in the form of solutions, suspensions, emulsions, lyophilizates or sterile powders.

For the other administration routes e.g. inhalation medicament forms (inter alia powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents are suitable.

Oral and parenteral administration are preferred, in particular oral and intravenous administration.

The compound of the formula (II) according to the invention can be converted into the administration forms mentioned. This can be effected in a manner known per se by mixing with inert, non-toxic, pharmaceutically suitable auxiliary substances. These auxiliary substances include inter alia carrier substances (for example microcrystalline cellulose, lactose, mannitol), solvents (e.g. liquid polyethylene glycols), emulsifiers and dispersing or wetting agents (for example sodium dodecyl sulphate, polyoxysorbitan oleate), binders (for example polyvinylpyrrolidone), synthetic and natural polymers (for example albumin), stabilizers (e.g. antioxidants, such as, for example, ascorbic acid), colorants (e.g. inorganic pigments, such as, for example, iron oxides) and flavour and/or odour correctants.

In general, it has been found to be advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, and in particular depending on the body weight, administration route, individual behaviour towards the active compound, nature of the formulation and point of time or interval at which administration takes place. Thus in some cases it may be sufficient to manage with less than the abovementioned minimum amount, while in other cases the upper limit mentioned must be exceeded. In the case where relatively large amounts are administered, it may be advisable to distribute these into several individual doses over the day.

The following working examples illustrate the invention. The invention is not limited to the examples.

The percentage data in the following tests and examples are percentages by weight, unless stated otherwise; parts are parts by weight. The solvent ratios, dilution ratios and concentration data of liquid/liquid solutions in each case relate to the volume.

A. EXAMPLES

| Abbreviations: | |
|---|---|
| ACN | acetonitrile |
| bS | broad singlet (in NMR spectra) |
| D | doublet (in NMR spectra) |
| DSC | differential scanning calorimetry |
| % by weight | percent by weight |
| M | multiplet (in NMR spectra) |
| n.d. | not detected |
| NMR | nuclear magnetic resonance |
| rh | relative humidity |
| S | singlet (in NMR spectra) |
| sec | seconds |
| T | triplet (in NMR spectra) |
| v/v | volume/volume |
| δ | deformational vibrations |
| ν | stretching vibrations |

Starting Materials

Example 1A

Methyl 2-(1H-1,2,3-triazol-1-yl)acrylate 450 g of ethyl 2-(1H-1,2,3-triazol-1-yl)acetate were dissolved in 3.5 l of methanol, 30 g of triethylamine were added and the mixture was stirred at 22° C. for 16 h. All solvents were then distilled off under reduced pressure. This gave 410 g of the title compound as an oil.

Example 2A

Methyl 3-(dimethylamino)-2-(1H-1,2,3-triazol-1-yl)acrylate 522 g of dimethylformamide dimethyl acetal were added to 400 g of methyl 2-(1H-1,2,3-triazol-1-yl)acrylate, and the mixture was heated to the boil. Low-boiling components formed were distilled off. After 4 h, the mixture was cooled to 55° C., and 1050 ml of methyl tert-butyl ether/2-propanol (3:1 v/v) were metered in. The resulting suspension was cooled to 22° C. and filtered. The filter cake was repeatedly washed with methyl tert-butyl ether and dried under reduced pressure at 40° C. This gave 493 g of the title compound as a solid.

Example 3A

1-[6-(Morpholin-4-yl)pyrimidin-4-yl]-4-(1H-1,2,3-triazol-1-yl)-1H-pyrazol-5-ol form; formula (Ia)) or 2-[6-(morpholin-4-yl)pyrimidin-4-yl]-4-(1H-1,2,3-triazol-1-yl)-1,2-dihydro-3H-pyrazol-3-one (keto form; formula (Ib))

5.84 g of trifluoroacetic acid were added to 20 g of 4-(6-hydrazinopyrimidin-4-yl)morpholine and 24.6 g of methyl (2E/Z)-3-(dimethylamino)-2-(1H-1,2,3-triazol-1-yl)acrylate in 210 ml of ethyl acetate, and the mixture was stirred under reflux for 24 h. The suspension obtained was cooled to 0° C. and filtered. The filter cake was washed with ethyl acetate, filtered off with high suction and then suspended in 160 ml of water. The suspension was adjusted to about pH 5 by addition of 4.5 ml of acetic acid, stirred for a further 15 minutes and filtered. The filter cake was washed twice with 50 ml of water and then dried under reduced pressure at 40° C. Yield: 26.0 g (79.4% of theory) of the title compound.

The preparation of the compounds 4-(6-hydrazinopyrimidin-4-yl)morpholine (Example No. 16A), ethyl 2-(1H-1,2,3-triazol-1-yl)acetate (Example No. 39A) and ethyl 3-(dimethylamino)-2-(1H-1,2,3-triazol-1-yl)acrylate (Example No. 3A) has already been described in WO 2008/067871.

The preparation of the compound 2-(6-morpholin-4-ylpyrimidin-4-yl)-4-(1H-1,2,3-triazol-1-yl)-1,2-dihydro-3H-pyrazol-3-one from 4-(6-hydrazinopyrimidin-4-yl)morpholine and ethyl 3-(dimethylamino)-2-(1H-1,2,3-triazol-1-yl) acrylate has also been described in WO 2008/067871 (Example No. 71).

Working Examples

Example 1

Sodium 1-[6-(morpholin-4-yl)pyrimidin-4-yl]-4-(1H-1,2,3-triazol-1-yl)-1H-pyrazol-5-olate (Compound of the Formula (II))

Example 1.1

10 g of the compound from Example 3A were suspended in 50 ml of methanol/water (9:1 v/v). With stirring, 3.4 g of 45% strength aqueous sodium hydroxide solution were added to the suspension, and a further 50 ml of methanol/water (9:1 v/v) were added. The suspension was warmed to 50° C. and stirred at 50° C. for 2 h. The mixture was then cooled to 0° C., stirred at 0° C. for another 1 h and filtered. The filter cake obtained was washed with methanol/water (9:1 v/v) and dried. Yield: 10.1 g of the compound of the formula (II); 6.8% by weight of Na Example 1.2

5 g of the compound from Example 3A were suspended in 60 ml of ethanol/water (1:1 v/v) and 1.41 g of 45% strength aqueous sodium hydroxide solution were added at 22° C. The suspension was stirred at 50° C. for 3 days and at 20° C. for 2 h. The solid was filtered off, washed with 10 ml of water and dried. Yield: 4 g of the compound of the formula (II).

Example 1.3

30.25 g of the compound from Example 3A were suspended in 150 ml of methanol/water (9:1 v/v) at 22° C. 13.3 ml of triethylamine were added, and the mixture was warmed to 60° C. After 15 min, the almost clear solution obtained was filtered, the filter was washed with 10 ml of methanol/water (9:1 v/v) and at 60° C. 10.3 g of 45% strength aqueous sodium hydroxide solution were added slowly to the filtrate collected. A few crystals of the compound of the formula (H) were added to the suspension obtained, and the mixture was stirred at 60° C. for 1 h and then slowly cooled to 0° C. and filtered. The filter cake was washed with 15 ml of methanol/water (9:1 v/v) and dried at 40° C. under reduced pressure. Yield: 25.1 g of the compound of the formula (H).

Example 1.4

25 g of the compound from Example 3A were suspended in 150 ml of methanol/water (1:1 v/v), and 11 ml of triethylamine were added. The solution obtained was warmed to 60° C., and 8.5 g of 45% strength aqueous sodium hydroxide solution were added. The suspension obtained was slowly cooled to 22° C., stirred at 22° C. for 2 h and then stirred at 0-5° C. for 1 h. After filtration the filter cake was washed with 15 ml of methanol/water (1:1 v/v) and dried at 40° C. under reduced pressure. Yield: 26 g of the compound of the formula (H).

Differential Scanning Calorimetry (DSC):

The thermograms were obtained using a DSC 7 or Pyris-1 differential scanning calorimeter and a TGA 7 thermogravimetric analyser from Perkin-Elmer.

DSC 7 or Pyris-1 Differential Scanning calorimeter; manufacturer: Perkin-Elmer; heating rate: 2 and 20 K/min: purge gas: nitrogen; crucible: aluminium crucible (not gas-tight); sample preparation: none.

TGA 7 Thermogravimetric Analyzer; manufacturer: Perkin-Elmer; heating rate: 10 Kmin$^{-1}$; purge gas: nitrogen, 20-30 ml/min; crucible: open platinum crucible; sample preparation: none.

Sodium 1-[6-(morpholin-4-yl)pyrimidin-4-yl]-4-(1H-1,2,3-triazol-1-yl)-1H-pyrazol-5-olate (compound of the formula (II)) decomposes above 300° C. without melting.

Vapour Adsorption and Vapour Desorption:

The moisture sorption isotherm was recorded using a Dynamic Vapour Sorption Analyzer IGA Sorp from Hiden Analytical. The measuring temperature was 25° C. There was no sample preparation.

TABLE 1

Vapour adsorption and vapour desorption of sodium 1-[6-(morpholin-4-yl)pyrimidin-4-yl]-4-(1H-1,2,3-triazol-1-yl)-1H-pyrazol-5-olate (compound of the formula (II))

| | Compound of the formula (II) | | Compound of the formula (I) | |
|---|---|---|---|---|
| Relative | Adsorption | Desorption | Adsorption | Desorption |
| 0% rh | 0% | 0% | 0.1% | 0.1% (5% rh) |
| 10% rh | 0% | 0% | 0.2% | 0.1% |
| 20% rh | 0.1% | 0% | 0.3% | 0.2% |
| 30% rh | 0.1% | 0.1% | 4.8% | 4.7% |
| 40% rh | 0.2% | 0.2% | 5.1% | 5.2% |
| 50% rh | 0.2% | 0.3% | 5.3% | 5.4% |
| 60% rh | 0.2% | 0.3% | 5.4% | 5.6% |
| 70% rh | 0.4% | 0.4% | 5.6% | 5.6% |
| 80% rh | 0.4% | 0.5% | 5.7% | 5.7% |
| 90% rh | 0.8% | 0.8% | 5.9% | 5.9% |

Solubility Data:

Method: Saturated solutions of the test substance were prepared by stirring a suspension in water at 25° C. for 16 hours. The suspensions obtained were then filtered, and the content in the filtrate was determined by HPLC.

TABLE 2

Solubilities in water

| | Compound of the formula (II) | Compound of the formula (I) |
|---|---|---|
| solubility in water at 25° C. [mg/100 ml] | 2800 | 14.3 |

IR and Raman Spectroscopy:

For measuring IR and Raman spectra of the compound of the formula (II), Bruker FT/IR-spectrometer IFS 66v and Bruker FT/Raman spectrometer MultiRAM with the following parameters were used:

| | IR | Raman |
|---|---|---|
| spectral resolution | 2 cm$^{-1}$ | 2 cm$^{-1}$ |
| number of individual measurements (scans) | 32 | 64 |
| wave number range | 4000-500 cm$^{-1}$ | 3500-200 cm$^{-1}$ |
| sample preparation | KBr disc | none |

TABLE 3

Assignment of characteristic vibrational bands in the IR and Raman spectra of the compound of the formula (II)

| Structural element | Position of IR bands (cm$^{-1}$) | Position of Raman bands (cm$^{-1}$) |
|---|---|---|
| ν =C—H | 3153-3006 | 3153-3010 |
| ν C—H | 2976-2855 | 2978-2856 |
| ν C=C, ν C=N | 1630-1439 | 1623-1401 |
| ν C—N | 1241 | 1244 |
| ν C—O | 1112 | 1118 |
| δ =C—H$_{in\ phase}$ | 987 | 988 |

For measuring IR and Raman spectra of the compound of the formula (I), Bruker FT/IR-spectrometer Vertex 80v and Bruker FT/Raman spectrometer MultiRAM with the following parameters were used:

| | IR | Raman |
|---|---|---|
| spectral resolution | 2 cm$^{-1}$ | 2 cm$^{-1}$ |
| number of individual measurements (scans) | 32 | 64 |
| wave number range | 4000-500 cm$^{-1}$ | 3500-100 cm$^{-1}$ |
| sample preparation | KBr disc | none |

TABLE 4

Assignment of characteristic vibrational bands in the IR and Raman spectra of the compound of the formula (I)

| Structural element | Position of IR bands (cm$^{-1}$) | Position of Raman bands (cm$^{-1}$) |
|---|---|---|
| ν O—H | 3441 | — |
| ν =C—H | 3135-3108 | 3134-3006 |
| ν C—H | 2965-2884 | 2967-2884 |
| ν C=C, ν C=N, δ C—H | 1636-1345 | 1650-1345 |
| ν C—O$_{ether}$ | 1257 | 1259 |

UV/VIS Spectroscopy:

UV/VIS spectra were measured on a Perkin Elmer spectrometer (Lambda 40P) using the following conditions or parameters:

cuvette: path length 1 cm; quartz glass wave number range: 200-800 nm slit width: 1 nm sample preparation: about 1 mg/100 ml acetonitrile/water 1:1 bands: 285; 249 nm for the compound of the formula (II) and 289.3; 248.2 nm for the compound of the formula (I)

TABLE 5

Calculation of the specific absorption and the molar absorption coefficient

| Compound of the formula | Solvent | Wavelength (nm) | Specific absorption $A^{1\%}_{1\,cm}$ (litre/g * cm) | Molar absorption coefficient $\epsilon$ (litre/mol * cm) |
|---|---|---|---|---|
| (I) | acetonitrile/water 1:1 | 249 | 1111 | 34928 |
| (II) | acetonitrile/water 1:1 | 284 | 501.2 | 16855 |

NMR Spectroscopy:

NMR spectra were recorded on a Bruker NMR spectrometer (Advance) using the following conditions or parameters:

Structural formulae of the compound of the formula (II) and of the compound of the formula (I) with assignment of the respective NMR signals

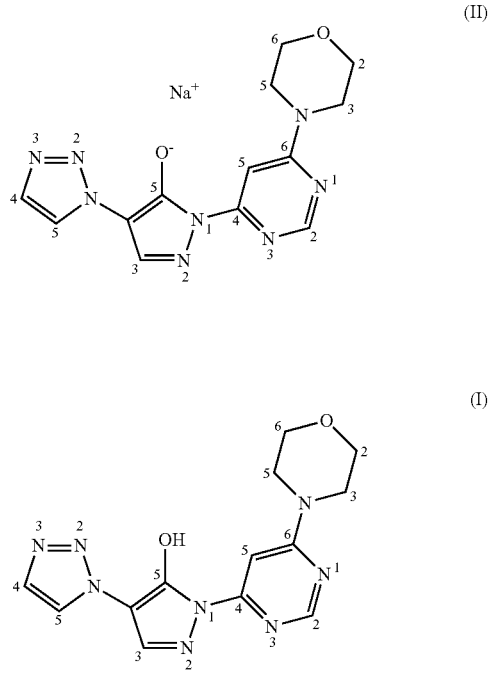 [SMILES: [O-]c1c(-n2ccnn2)cnn1-c1cc(N2CCOCC2)ncn1 ; [Na+] ; Oc1c(-n2ccnn2)cnn1-c1cc(N2CCOCC2)ncn1]

|  | $^1$H NMR spectrum | $^{13}$C NMR spectrum |
|---|---|---|
| Compound of the formula (II) | | |
| operating frequency | 500.13 MHz | 125.76 MHz |
| solvent | trifluoroaetic acid | trifluoroaetic acid |
| concentration | 6.84 mg/ml | 42.7 mg/ml |
| internal standard | tetramethylsilane (TMS) | tetramethylsilane (TMS) |
| sample tube diameter | 5 mm | 5 mm |
| temperature | 25° C. | 25° C. |
| technique | Fourier transfomation technique | Fourier transfomation technique |
| spectral width | 20.65 ppm | 245.41 ppm |
| digital resolution | 0.079 Hz/Pt | 0.4710 Hz/Pt |
| pulse duration | 2.83 μsec, excitation angle 30° | 9.1 μsec, excitation angle 90° |
| recording time | 6.399 sec | 1.06 sec |
| relaxation time | 0.5 sec | 4 sec |
| no. of free induction decays | 32 | 128 |
| Compound of the formula (I) | | |
| operating frequency | 500.13 MHz | 125.76 MHz |
| solvent | dimethyl sulphoxide-$d_6$ (DMSO) | dimethyl sulphoxide-$d_6$ (DMSO) |
| concentration | 6.3 mg/ml | 35.8 mg/ml |
| internal standard | tetramethylsilane (TMS) | tetramethylsilane (TMS) |
| sample tube diameter | 5 mm | 5 mm |
| temperature | 25° C. | 27° C. |
| technique | Fourier transfomation technique | Fourier transfomation technique |
| spectral width | 20.65 ppm | 240.89 ppm |
| digital resolution | 0.079 Hz/Pt | 0.9248 Hz/Pt |
| pulse duration | 3.1 μsec, excitation angle 30° | 7.0 μsec, excitation angle 90° |
| recording time | 6.344 sec | 1.08 sec |
| relaxation time | 0.5 sec | 4 sec |
| no. of free induction decays | 32 | 1024 |

TABLE 6

$^1$H NMR spectrum of the compound of the formula (II) - chemical shift, signal multiplicity, relative proton number (the numbering of the H atoms is based on the structural formula for assignment of the respective NMR signals)

| H atoms | Chem. shift δ (ppm) | Multiplicity and coupling constants | Number of protons/molecule |
|---|---|---|---|
| sodium 1-[6-(morpholin-4-yl) | | | |
| H-2; H-3; H-5; H-6 | 4.00-4.25 | M | 8 |
| pyrimidin-4-yl]- | | | |
| H-2 | 8.72 | S | 1 |
| H-5 | 7.77 | S | 1 |
| 4-(1H-1,2,3-triazol-1-yl)- | | | |
| H-4 | 8.64 | D J = 1.4 Hz | 1 |
| H-5 | 8.98 | D J = 1.4 Hz | 1 |
| 1H-pyrazol-5-olate | | | |
| H-3 | 8.68 | S | 1 |

TABLE 7

$^1$H NMR spectrum of the compound of the formula (I) - chemical shift, signal multiplicity, relative proton number (the numbering of the H atoms is based on the structural formula for assignment of the respective NMR signals)

| H atoms | Chem. shift δ (ppm) | Multiplicity and coupling constants | Number of protons/molecule |
|---|---|---|---|
| 1-[6-(morpholin-4-yl) | | | |
| H-2; H-3; H-5; H-6 | 3.71 | S | 8 |
| pyrimidin-4-yl]- | | | |
| H-2 | 8.55 | S | 1 |
| H-5 | 7.42 | S | 1 |
| 4-(1H-1,2,3-triazol-1-yl)- | | | |
| H-4 | 7.86 | D (0.6 Hz) | 1 |
| H-5 | 8.38 | D (0.6 Hz) | 1 |
| 1H-pyrazol-5-ol | | | |
| H-3 | 8.27 | S | 1 |
| 5-OH | n.d (c) | n.d. | 1 |

TABLE 8

$^{13}$C NMR spectrum of the compound of the formula (II) - chemical shift, signal multiplicity, relative number of C nuclei in the compound of the formula (II) (the numbering of the C atoms is based on the structural formula for assignment of the respective NMR signals)

| C atoms | Chem. shift δ (ppm) | Multiplicity and coupling constants | Number of C nuclei/molecule |
|---|---|---|---|
| sodium 1-[6-(morpholin-4-yl) | | | |
| C-2; C-6 | 67.80 | T | 2 |
| C-3; C-5 | 48.21 | T | 2 |
| pyrimidin-4-yl]- | | | |
| C-2 | 151.65 | D | 1 |
| C-4 | 152.01 | S | 1 |
| C-5 | 91.48 | D | 1 |
| C-6 | 159.90 | S | 1 |
| 4-(1H-1,2,3-triazol-1-yl)- | | | |
| C-4 | 130.93 | D | 1 |
| C-5 | 129.57 | D | 1 |
| 1H-pyrazol-5-olate | | | |
| C-3 | 138.03 | D | 1 |
| C-4 | 106.99 | S | 1 |
| C-5 | 157.43 | S | 1 |

TABLE 9

$^{13}$C NMR spectrum of the compound of the formula (I) - chemical shift, signal multiplicity, relative number of C nuclei in the compound of the formula (I) (the numbering of the C atoms is based on the structural formula for assignment of the respective NMR signals)

| C Atoms | Chem. shift δ (ppm) | Multiplicity and coupling constants | Number of C nuclei/molecule |
|---|---|---|---|
| 1-[6-(morpholin-4-yl | | | |
| C-2; C-6 | 65.56 | T | 2 |
| C-3, C-5 | 44.29 | T | 2 |
| pyrimidin-4-yl]- | | | |
| C-2 | 154.08 | D | 1 |
| C-4 | 152.43 | S | 1 |
| C-5 | 85.62 | D | 1 |
| C-6 | 161.99 | S | 1 |
| 4-(1H-1,2,3-triazol-1-yl)- | | | |
| C-4 | 132.94 | D | 1 |
| C-5 | 123.68 | D | 1 |
| 1H-pyrazol-5-ol | | | |
| C-3 | 135.84 | D | 1 |
| C-4 | 102.82 | S | 1 |
| C-5 | 154.70 | S | 1 |

Mass Spectroscopy:

The mass spectrum was recorded on a Waters mass spectrometer (ZQ) using the conditions or parameters listed below:

| Ionization method | ESI (electronic spray ionization) |
|---|---|
| Solvents | acetonitrile/water |

TABLE 10

Interpretation of the compound of the formula (II)

| | | Mass number (A) |
|---|---|---|
| Ion formation M + H | C13H14N8O2 + H | 315 |
| Ion formation M + Na | C13H14N8O2 + Na | 337 |

TABLE 11

Interpretation of the mass spectrum of the compound of the formula (I)

| | | Mass number (A) |
|---|---|---|
| Ion formation M + H | C13H15N8O2 | 315 |

Elemental Analysis:

TABLE 12

Results of the elemental analysis of the compound of the formula (II)

| Element | Measured (%) | Calculated (%) | Difference (%) |
|---|---|---|---|
| C | 46.1 | 46.4 | 0.3 |
| H | 4.0 | 3.9 | 0.1 |
| N | 33.1 | 33.3 | 0.2 |

TABLE 13

Results of the elemental analysis of the compound of the formula (I)

| Element | Measured (%) | Calculated (%) | Difference (%) |
|---|---|---|---|
| C | 49.5 | 49.7 | 0.2 |
| H | 4.4 | 4.5 | 0.1 |
| N | 35.5 | 35.7 | 0.2 |
| O | 12.6 | 10.2 | 2.4 |

X-Ray Diffractometry:

Transmission diffractometer PANalytical X'Pert PRO with PIXcel counter (multichannel):

| radiation: | copper, K alpha |
|---|---|
| primary monochromator: | focussing X-ray mirror |
| wavelength (K1): | 1.5406 Å |
| wavelength (K2): | 1.5444 Å |
| generator parameters: | 40 kV, 40 mA |
| measuring range: | 2-38° |
| room conditions: | 25° C., 40-60% rh | or

STOE powder diffraction system:

| diffractometer: | transmission |
|---|---|
| monochromator: | curved germanium (111) |
| generator: | 45 kV, 35 mA |
| wavelength: | 1.540598 Cu |
| detector: | linear PSD |
| scan mode: | transmission/moving PSD/fixed omega |
| scan type: | 2theta:omega |
| room conditions: | 25° C., 40-60% rh |

TABLE 14

X-ray powder diffractometry of the compound of the formula (II)
Compound of the formula (II)
reflexes [2 theta]

| | |
|---|---|
| 5.7 | 23.6 |
| 11.5 | 25.3 |
| 13.2 | 26.4 |
| 13.7 | 26.9 |
| 15.8 | 27.7 |
| 16.4 | 27.7 |
| 18.4 | 29.4 |
| 18.9 | 29.9 |
| 19.3 | 30.0 |
| 21.0 | 30.7 |
| 22.0 | 31.5 |
| 23.1 | 31.6 |

TABLE 15

X-ray powder diffractometry of the compound of the formula (I)
Compound of the formula (I)
reflexes [2 theta]

| | |
|---|---|
| 5.6 | 24.6 |
| 14.4 | 24.8 |
| 14.9 | 25.1 |
| 16.3 | 26.3 |
| 16.5 | 26.8 |
| 17.6 | 28 |
| 17.8 | 28.5 |
| 18.2 | 29 |
| 18.5 | 29.9 |
| 19 | 32.4 |
| 19.7 | 32.7 |
| 21.6 | 33.2 |
| 22 | 33.8 |
| 22.4 | 34.7 |
| 22.9 | 35.7 |
| 24 | 36.4 |
| 24.5 | 36.7 |

B. EVALUATION OF THE PHARMACOLOGICAL ACTIVITY

The pharmacological properties of the compounds according to the invention can be demonstrated in the following assays:

| Abbreviations: | |
|---|---|
| DMEM | Dulbecco's modified Eagle Medium |
| FCS | fetal calf serum |
| TMB | 3,3',5,5'-tetramethylbenzidine |
| Tris | tris(hydroxymethyl)aminomethane |

1. In vitro Tests for Determination of the Activity and Selectivity of HIF Prolyl 4-Hydroxylase Inhibitors 1.a) Inhibition of the activity of HIF prolyl hydroxylase:

Hydroxylated HIF bonds specifically to the von Hippel-Lindau protein-elongin B-elongin C complex (VBC complex). This interaction occurs only if HIF is hydroxylated on a conserved prolyl radical. It is the basis for the biochemical determination of HIF prolyl hydroxylase activity. The test is carried out as described [Oehme F., Jonghaus W., Narouz-Ott L., Huetter J., Flamme I., *Anal. Biochem.* 330 (1), 74-80 (2004)]:

A clear 96-well microtiter plate coated with NeutrAvidin HBC (Pierce) is incubated with blocker casein for 30 minutes. The plate is then washed three times with 200 µl each time of wash buffer (50 mM Tris, pH 7.5, 100 mM NaCl, 10% (v/v) blocker casein, 0.05% (v/v) Tween 20) per well. The peptide biotin-DLDLEMLAPYIPMDDDFQL (Eurogentec, 4102 Seraing, Belgium) is added in a concentration of 400 nM in 100 µl wash buffer. This peptide serves as a substrate for the prolyl hydroxylation and is bonded to the microtiter plate. After incubation for 60 minutes, the plate is washed three times with wash buffer, incubated with 1 mM biotin in blocker casein for 30 minutes and then washed again three times with wash buffer.

To carry out the prolyl hydroxylase reaction, the peptide substrate bonded to the plate is incubated with a cell lysate containing prolyl hydroxylase for 1 to 60 minutes. The reaction takes place in 100 µl reaction buffer (20 mM Tris, pH 7.5, 5 mM KCl, 1.5 mM $MgCl_2$, 1 µM-1 mM 2-oxoglutarate, 10 µM $FeSO_4$, 2 mM ascorbate) at room temperature. The reaction mixture moreover contains various concentrations of the prolyl hydroxylase inhibitor to be tested. The test substance is preferably, but not exclusively, employed at concentrations of between 1 nM and 100 µM. The reaction is stopped by washing the plate three times with wash buffer.

For quantitative determination of the prolyl hydroxylation, a fusion protein which contains both thioredoxin from *E. coli* and the VBC complex in 80 µl bonding buffer (50 mM Tris, pH 7.5, 120 mM NaCl) is added. After 15 minutes, 10 µl of a solution of polyclonal anti-thioredoxin antibodies from rabbit in bonding buffer are added. After a further 30 minutes, 10 µl of a solution of anti-rabbit immunoglobulin coupled to horseradish peroxidase in bonding buffer are added. After incubation at room temperature for 30 minutes, the plate is washed three times with wash buffer in order to remove non-bonded VBC complex and antibodies. To determine the amount of bonded VBC complex, the plate is incubated with TMB for 15 minutes. The colour reaction is ended by addition of 100 µl 1 M sulphuric acid. The amount of bonded VBC complex is determined by measurement of the optical density at 450 nm. It is proportional to the amount of hydroxylated proline in the peptide substrate.

Alternatively, a VBC complex coupled to europium (Perkin Elmer) can be used for detection of the prolyl hydroxylation. In this case, the amount of bonded VBC complex is determined by the fluorescence with respect to time. The use of VBC complex labelled with [$^{35}$S]-methionine is moreover possible. For this, the radioactively labelled VBC complex can be prepared by in vitro transcription-translation in reticulocyte lysate.

The compound of the formula (II) according to the invention inhibits the activity of HIF prolyl hydroxylase in this test with an $IC_{50}$ value of 0.47 µM (mean for EGLN2/PHD1) or 0.14 µM (mean for EGLN1/PHD2).

1.b) Cellular, Functional in vitro Test:

The activity of the compounds according to the invention is quantified with the aid of a recombinant cell line. The cell is originally derived from a human lung carcinoma cell line (A549, ATCC: American Type Culture Collection, Manassas, Va. 20108, USA). The test cell line is transfected in a stable manner with a vector which contains the reporter gene of *Photinus pyralis* luciferase (called luciferase in the following) under the control of an artificial minimal promoter. The minimal promoter comprises two hypoxia-responsible elements upstream of a TATA box [Oehme F., Ellinghaus P., Kolkhof P., Smith T. J., Ramakrishnan S., Hüter J., Schramm M., Flamme I., *Biochem. Biophys. Res. Commun.* 296 (2), 343-9 (2002)]. Under the effect of hypoxia (e.g. culturing in the presence of 1% oxygen for 24 hours) or under the action of non-selective dioxygenase inhibitors (e.g. desferroxamine in a concentration of 100 µM, cobalt chloride in a concentration of 100 µM or N-oxalylglycine diethyl ester in a concentration of 1 mM), the test cell line produces luciferase, which can be detected and quantified with the aid of suitable bioluminescence reagents (e.g. Steady-Glo® Luciferase Assay System, Promega Corporation, Madison, Wis. 53711, USA) and a suitable luminometer.

Test Procedure:

On the day before the test, the cells are plated out in an exactly calculated amount of culture medium (DMEM, 10% FCS, 2 mM glutamine) in 384- or 1,536-well microtiter plates and kept in a cell incubator (96% atmospheric humidity, 5% v/v $CO_2$, 37° C.). On the test day, the test substances are added to the culture medium in graduated concentrations. No test substance is added to the cells in batches serving as negative controls. As a positive control for determination of the sensitivity of the cell to inhibitors, e.g. desferroxamine is added in a final concentration of 100 µM. Six to 24 hours after transfer of the test substances into the wells of the microtiter plates, the resulting light signal is measured in the luminometer. A dose/effect relationship is plotted with the aid of the measurement values, which serves as a basis for determining the half-maximum active concentration (called the $EC_{50}$ value).

In the test described herein, the compound of the formula (II) according to the invention has an $EC_{50}$ value of 7 nM.

1.c) Cellular, Functional in vitro Test of Modification of the Gene Expression:

To investigate the modification of the expression of specific mRNAs in human cell lines after treatment with test substances, the following cell lines are cultured on 6- or 24-well plates: human hepatoma cells (HUH, JCRB Cell Bank, Japan), human embryonal kidney fibroblasts (HEK/293, ATCC, Manassas, Va. 20108, USA), human cervical carcinoma cells (HeLa, ATCC, Manassas, Va. 20108, USA), human umbilical vein endothelial cells (HUVEC, Cambrex, East Rutherford, N.J. 07073, USA). 24 hours after addition of the test substances, the cells are washed with phosphate-buffered saline and the total RNA is obtained from them using a suitable method (e.g. Trizol® reagent, Invitrogen GmbH, 76131 Karlsruhe, Germany).

For a typical analysis experiment, 1 µg each of the total RNA obtained in this way is digested with DNase I and translated into a complementary DNA (cDNA) using a suitable reverse transcriptase reaction (ImProm-II Reverse Transcription System, Promega Corporation, Madison, Wis. 53711, USA). 2.5% of the cDNA batch obtained in this way is used in each case for the polymerase chain reaction. The expression level of the mRNA of the genes to be investigated is investigated by means of the real time quantitative polymerase chain reaction [TaqMan-PCR; Heid C. A., Stevens J., Livak K. J., Williams P. M., Genome Res. 6 (10), 986-94 (1996)] using an ABI Prism 7700 sequence detection instrument (Applied Biosystems, Inc.). The primer-probe combinations used here are generated by means of Primer Express 1.5 Software (Applied Biosystems, Inc.). Specifically, the mRNAs of erythropoietin, carboanhydrase IX, lactate dehydrogenase A and vascular endothelial cell growth factor are investigated.

2. In vivo Tests for Detection of the Action in the Cardiovascular System 2.a) In vivo test of Modification of Gene Expression:

The test compounds dissolved in suitable solvents are administered to mice or rats either orally by stomach tube administration, intraperitoneally or intravenously. Typical dosages are 0.1, 0.5, 1, 5, 10, 20, 50, 100 and 300 mg substance per kg of body weight and administration. Control animals receive only solvent. 4, 8 or 24 hours after administration of the test substance the animals are sacrificed with an overdose of isoflurane and a subsequent fracture of the neck and the organs to be investigated are removed. Parts of the organs are shock-frozen in liquid nitrogen. Total RNA is obtained from the organ parts as described under B.1.a) and this is translated into a cDNA. The expression level of the mRNA of the genes to be investigated is investigated by means of the real time quantitative polymerase chain reaction [TaqMan-PCR; Heid C. A., Stevens J., Livak Williams P. M., Genome Res. 6 (10), 986-94 (1996)] using an ABI Prism 7700 sequence detection instrument (Applied Biosystems, Inc.).

The substance according to the present invention leads to a significant dose-dependent increase in the mRNA of erythropoietin in the kidney after oral or parenteral administration compared with the placebo control.

2.b) Determination of the Erythropoietin Level in Serum:

The test substance in a suitable solvent is administered to mice or rats either intraperitoneally or orally once or twice daily. Typical dosages are 0.1, 0.5, 1, 5, 10, 20, 50, 100 and 300 mg substance per kg of body weight and administration. Placebo control animals receive only solvent. Before the administration and four hours after the last administration of substance, blood is taken from the animals from the retroorbital venous plexus or the tail vein under short narcosis. The blood is rendered uncoagulable by addition of lithium heparin. The blood plasma is obtained by centrifugation. The content of erythropoietin in the blood plasma is determined with the aid of an erythropoietin-ELISA (Quantikine® mouse Epo Immunoassay, R&D Systems, Inc., Minneapolis, USA) in accordance with the manufacturer's instructions. The measurement values are converted into pg/ml with the aid of a reference measurement recorded for mouse erythropoietin.

The substances according to the present invention leads to a significant dose-dependent increase in the plasma erythropoietin after oral and parental administration compared with the starting value and the placebo control.

2.c) Determination of the Cell Composition of Peripheral Blood:

The test substance in a suitable solvent is administered to mice or rats either intraperitoneally or orally once or twice daily for several days. Typical dosages are e.g. 0.1, 0.5, 1, 5, 10, 20, 50, 100 and 300 mg substance per kg of body weight and administration. Control animals receive only solvent. At the end of the study, blood is taken from the animals from the venous plexus of the corner of the eye or the tail vein under short narcosis and is rendered uncoagulable by addition of sodium citrate. The concentrations of erythrocytes, leukocytes and thrombocytes are determined in the blood samples in a suitable electronic measuring apparatus. The concentration of the reticulocytes is determined by microscope screening of in each case 1000 erythrocytes with the aid of blood smears stained with a stain solution suitable for this purpose (KABE Labortechnik, Nübrecht). For determination of the haematocrit, blood is taken from the retroorbital venous plexus by means of a haematocrit capillary and the haematocrit value is read off manually after centrifugation of the capillary in a centrifuge suitable for this purpose.

The substance according to the present invention leads to a significant dose-dependent increase in the haematocrit, the erythrocyte count and the reticulocytes after oral and parenteral administration compared with the starting value and the placebo control.

C. WORKING EXAMPLES FOR PHARMACEUTICAL COMPOSITIONS

The compounds according to the invention can be converted into pharmaceutical formulations as follows:

Tablet:
Composition:
100 mg of the compound according to the invention, 50 mg lactose (monohydrate), 50 mg maize starch (native), 10 mg polyvinylpyrrolidone (PVP 25) (BASF, Ludwigshafen, Germany) and 2 mg magnesium stearate.

Tablet weight 212 mg. Diameter 8 mm, radius of curvature 12 mm

Preparation:
The mixture of compound according to the invention, lactose and starch is granulated with a 5% strength solution (w/w) of the PVP in water. After drying, the granules are mixed with the magnesium stearate for 5 minutes. This mixture is pressed with a conventional tablet press (for tablet format see above). A pressing force of 15 kN is used as the recommended value for the pressing.

Suspension for Oral Administration:
Composition:
1000 mg of the compound according to the invention, 1000 mg ethanol (96%), 400 mg Rhodigel® (xanthan gum from FMC, Pennsylvania, USA) and 99 g water.

10 ml of oral suspension correspond to an individual dose of 100 mg of the compound according to the invention.

Preparation:
The Rhodigel is suspended in ethanol and the compound according to the invention is added to the suspension. The water is added with stirring. The mixture is stirred for approx. 6 h until swelling of the Rhodigel has ended.

Solution for Oral Administration:
Composition:
500 mg of the compound according to the invention, 2.5 g polysorbate and 97 g polyethylene glycol 400. 20 g of oral solution correspond to an individual dose of 100 mg of the compound according to the invention.

Preparation:
The compound according to the invention is suspended in a mixture of polyethylene glycol and polysorbate, while stirring. The stirring operation is continued until dissolution of the compound according to the invention is complete.

i.v. Solution:
The compound according to the invention is dissolved in a concentration below the saturation solubility in a physiologically acceptable solvent (e.g. isotonic saline solution, glucose solution 5% and/or PEG 400 solution 30%). The solution is subjected to sterile filtration and is transferred into sterile and pyrogen-free injection containers.

The invention claimed is:

1. Sodium 1-[6-(morpholin-4-yl)pyrimidin-4-yl]-4-(1H-1,2,3-triazol-1-yl)-1H-pyrazol-5-olate corresponding to the compound of the formula (II)

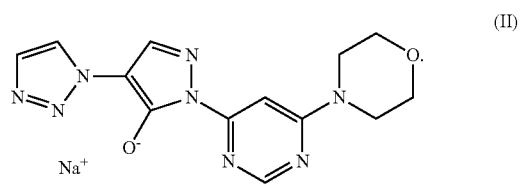 [SMILES: [O-]c1c(-n2ccnn2)cnn1-c1cc(N2CCOCC2)ncn1 ; [Na+]]

2. Compound of the formula (II) according to claim 1, wherein the compound of the formula (II) is present in crystalline form.

3. Process for preparing the compound of the formula (II) according to claim 1, comprising reacting the compound of the formula (I)

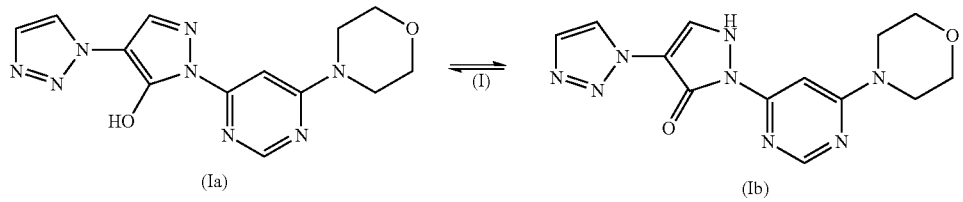 [SMILES: Oc1c(-n2ccnn2)cnn1-c1cc(N2CCOCC2)ncn1 ; "(I)" ; O=c1c(-n2ccnn2)c[nH]n1-c1cc(N2CCOCC2)ncn1]

in a solvent with sodium hydroxide or aqueous sodium hydroxide solution or a sodium salt, optionally with the addition of a base.

4. Process for preparing the compound of the formula (II) according to claim 3, comprising reacting the compound of the formula (I) in a solvent with aqueous sodium hydroxide solution, optionally with the addition of a base.

5. Process for preparing the compound of the formula (II) according to claim 3, comprising reacting the compound of the formula (I) in a solvent with aqueous sodium hydroxide solution with the addition of triethylamine.

6. A pharmaceutical composition comprising the compound according to claim 1 in combination with an inert, non-toxic, pharmaceutically suitable auxiliary.

7. A pharmaceutical composition comprising the compound according to claim 1 in combination with a further active compound.

8. A pharmaceutical composition comprising the compound according to claim 2 in combination with an inert, non-toxic, pharmaceutically suitable auxiliary.

9. A pharmaceutical composition comprising the compound according to claim 2 in combination with a further active compound.

* * * * *